(12) United States Patent
Segura et al.

(10) Patent No.: US 6,890,556 B1
(45) Date of Patent: May 10, 2005

(54) CONTROLLED SURFACE-ASSOCIATED DELIVERY OF GENES AND OLIGONUCLEOTIDES

(75) Inventors: Tatiana Segura, Evanston, IL (US); Lonnie D. Shea, Evanston, IL (US)

(73) Assignee: Northwestern University, Evanston, IL (US)

(*) Notice: Subject to any disclaimer, the term of this patent is extended or adjusted under 35 U.S.C. 154(b) by 235 days.

(21) Appl. No.: 10/076,060

(22) Filed: Feb. 14, 2002

Related U.S. Application Data

(60) Provisional application No. 60/268,626, filed on Feb. 14, 2001.

(51) Int. Cl.$^7$ ............................................. A61K 9/127
(52) U.S. Cl. .................... 424/450; 435/458; 435/320.1; 536/23.1
(58) Field of Search .......................... 424/450; 435/458, 435/320.1; 536/23.1

(56) References Cited

U.S. PATENT DOCUMENTS

| | | | |
|---|---|---|---|
| 6,312,727 B1 | 11/2001 | Schacht et al. | |
| 6,544,790 B1 * | 4/2003 | Sabatini | ..................... 435/455 |
| 2002/0197720 A1 | 12/2002 | Uhler | |
| 2003/0077827 A1 | 4/2003 | Uhler | |

OTHER PUBLICATIONS

Adami et al., J. Pharm. Sci., 87:678–683 (1998).
Bonadio et al., Nat. Med., 5:753–759 (1999).
Bielinska et al., Biomaterials,21:877–887 (2000).
Bielinska et al., Biochim. Biophys. Acta, 1353:180–190 (1997).
Duguid et al., Biophys J., 74:2802–2814 (1998).
Fischer et al., Pharm. Res., 16:1273–1279 (1999).
Gao et al., Biochemistry, 35:1027–1036 (1996).
Luo et al., Nat. Biotechnol., 18:893–895 (2000).
Shea et al., Nat. Biotechnol., 17:551–554 (1999).
Vitiello et al., Gene Ther., 3:396–404 (1996).
Zheng et al., Biotechnol. Prog., 16:254–257 (2000).

* cited by examiner

Primary Examiner—James Ketter
(74) Attorney, Agent, or Firm—Klauber & Jackson

(57) ABSTRACT

A system and method for controlled gene delivery comprising condensed nucleic acids complexed with polylinkers, wherein the complexes are covalently and/or non-covalently bound to the surface of a substrate capable of supporting cell adhesion. The gene delivery system achieves temporal and spatial control of nucleic acid delivery to a target cell or cells through control of complex density on the surface of the support substrate, and reversibility of the attachment of the polylinker to the support substrate. The system and method of the invention can be used to create spatial patterns of gene expression, and in tissue engineering, high throughput screening, and gene therapy applications.

29 Claims, 9 Drawing Sheets

CONTROLLED SURFACE-ASSOCIATED DELIVERY OF GENES AND OLIGONUCLEOTIDES

CROSS-REFERENCE TO RELATED APPLICATIONS

The present application is a non-provisional application which claims the priority of provisional application U.S. Ser. No. 60/268,626, filed on Feb. 14, 2001 now abandoned, the disclosure of which is hereby incorporated by reference in its entirety. Applicants claim the benefits of this application under 35 U.S.C. §119(e).

FIELD OF THE INVENTION

The present invention relates to methods for the controlled delivery of a nucleic acid into a cell. More specifically, the invention relates to methods of targeting and controlling the delivery of a nucleic acid to a cell or cell population with a system comprising DNA complexed to a polylinker which is attached to a support substrate.

BACKGROUND OF THE INVENTION

Developing systems capable of controlled and efficient gene transfer is a fundamental goal of biotechnology, with applications ranging from basic science to clinical medicine. Increasing or decreasing the expression level of a gene within a cell has the power to reveal or confirm the roles of specific components of signaling pathways and can lead to a mechanistic understanding of cell behavior, disease pathogenesis, and drug action. The successful application of gene transfer for basic science and clinical medicine requires the ability to manipulate the expression of target genes in the desired cell population. A variety of approaches are being taken to develop techniques to overcome barriers to gene transfer, which includes processes such as cellular internalization, endosomal escape, and nuclear trafficking.

Cationic polymers provide a versatile approach for gene transfer as the polymers can be designed or modified to overcome some of the current problems encountered with gene transfer. Complexation with cationic polymers functions to condense DNA, to produce a complex with a less-negative surface charge, to enhance cellular internalization of DNA, and to protect the DNA from degradation. Although many types of cationic polymers have been explored (see, for example, van de Wetering et al. (1999) Bioconjug. Chem. 10:589–597), polymers based on poly(L-lysine) (PLL) (see, for example, Choi et al. (1999) Bioconjug. Chem. 10:62–65), poly(ethylenimine) (PEI) (see, for example, Blessing et al. (2001) Bioconjug. Chem. 12:529–537), poly(amidoamine) (PAMAM) (see, for example, Qin et al. (1998) Hum. Gene Ther. 9:553–560), and poly(2-dimethylamino)ethylmethacrylate (p(DMAEMA)) (Arigita et al. (1999) Pharm. Res. 16:1534–1541) are among those utilized.

PEI covalently attached to a biodegradable polymer surface and to surface-immobilized collagen has been used as a gene delivery system. For example, Zheng et al. (2000) Biotechnol. Prog. 16:254–257, created a polymer surface with attached PLL and PEI, to which DNA was non-specifically adsorbed for delivery into a cell.

Recently, polymeric systems originally developed to deliver biologically active proteins have been adapted to deliver non-viral DNA. Polymeric scaffolds have been fabricated from a variety of materials, both natural (e.g., collagen) and synthetic (e.g., poly(lactide-co-glycolide)) which function as a support for cell adhesion and migration. These scaffolds act to increase the local concentration of DNA within the cellular microenvironment either by providing a sustained release of DNA (Shea et al. (1999) Nat. Biotechnol. 17:551–554) or by maintaining the DNA locally (Bonadio et al. (1999) Nat. Med. 5:753–759). Bielinska et al. (2000) Biomaterials 21:877–887 describe the use of a solid support membrane as a device for DNA delivery mediated by PAMAM dendrimers to skin cells. Synthetic systems have also been developed that increase cell-surface concentrations of DNA by adsorbing DNA complexes to the surface (Luo et al. (2000) Nat. Biotechnol. 18:893–895). U.S. Pat. No. 6,312,727 describes a nucleic acid delivery vehicle in which complexes formed from nucleic acids condensed with cationic polymer material are reacted with hydrophilic polymer material to form a hydrophilic coating or shield around the complex.

SUMMARY OF THE INVENTION

The present invention is a novel system for the controlled delivery of a nucleic acid to a target cell or cells that combines nucleic acid condensation with polymeric delivery by tethering or immobilizing nucleic acid complexes to a surface that supports cell adhesion. The gene delivery system of the invention allows both temporal and spatial control of gene delivery due to efficient internalization of the immobilized complex, elevated DNA concentrations in the microenvironment of cells adhered to the support substrate, and through alterations in the number of tether to the complexes and reversibility of complex immobilization.

Accordingly, in a first aspect, the invention features a controlled nucleic acid delivery system comprising nucleic acid-polylinker complexes tethered or immobilized to a support substrate, wherein the nucleic acid-polylinker complex is capable of being delivered or internalized by a cell adhering to the support substrate.

The nucleic acid-polylinker complexes are immobilized to the surface of a support substrate by a functional group attached to the polylinker. A polylinker modified by a functional group may attach to the support substrate directly or may attach through a modifying functional group present on the support substrate. The polylinker may be modified with a functional group before or after formation of the complex, but the complex must be formed prior to attachment to the solid support. The polylinker may be modified with a functional group before or after formation of the complex, but the complex must be formed prior to attachment to the solid support.

The complexes may be covalently or non-covalently immobilized. In one embodiment, the complexes are covalently attached to the support substrate. In this embodiment, the complexes may be formed by condensation of the nucleic acid with a non-modified polylinker. The complex is then reacted with a functional group on the support substrate to generate a covalent bond between the polylinker and the support substrate. In another embodiment of the covalent attachment of the complexes to the support substrate, the nucleic acid is condensed with a modified polylinker. The resulting complex is then reacted with a functional group on the solid support to generate a covalent bond between the polylinker and the support substrate. In another embodiment, the complexes are non-covalently immobilized to the support substrate. In this embodiment, the complexes may be formed by condensation of the nucleic acid with a non-modified polylinker. The complex is then modified with a functional group that will specifically interact with a functional group on the solid support to generate a non-covalent bond. In another embodiment of the non-covalent attachment of the complexes to the support substrate, the nucleic acid is condensed with a modified polylinker. The complex is then reacted with a functional group on the solid support to generate a non-covalent bond. In one embodiment, more than 0.2% of the immobilized complexes are bonded to the support substrate. In a specific embodiment, a covalent bond between a polylinker and the support substrate is broken after a cell is plated on the support surface.

In specific embodiments, the nucleic acid is DNA, RNA, or an oligonucleotide. In a more specific embodiment, the oligonucleotide is an antisense oligonucleotide or catalytic RNA capable of interfering with the expression of a gene. In another more specific embodiment, the DNA or RNA directs the intracellular expression of a gene.

In more specific embodiments, the polylinker is a cationic polymer, cationic lipid, cationic protein, or cationic peptide. In a specific embodiment, the polylinker is a cationic polymer or cationic peptide.

The support substrate of the invention is any substrate capable of supporting cell adhesion. In more specific embodiments, the support substrate is glass, collagen, peptide polymers, polysaccharide polymers, carbohydrate, polymers, polystyrene, lipid, metal, plastic, alumina gels, nitrocellulose, nylon membranes, cotton, or glass wool. The support substrate either contains or can be chemically modified to contain a functional group that allows the support substrate to covalently bind to a bifunctional crosslinker or polylinker modified to have a functional group.

In the controlled nucleic acid delivery system of the invention, nucleic acid delivery is controlled through (i) complex density at the surface of the support substrate, (ii) complex location on the surface of the support substrate, and (iii) the number of bonds linking the polylinkers in the complex to the support substrate. In one embodiment, the bonds between the polylinkers and the support substrate are reversible. In a specific embodiment, complex density on the surface of the support substrate ranges from 0.01 to 10.0 $\mu$g DNA/cm$^2$; and in a more specific embodiment, from 0.05 to 5.0 $\mu$g DNA/cm$^2$.

The relative strength of the attachment between the immobilized complex and the support substrate, and the reversibility of complex immobilization at the surface of the support substrate are factors that determine the release rate of a complex from the support substrate, and the availability of the released complex for internalization, e.g., delivery, to a cell or cell population.

In a second aspect, the invention features a method of controlled nucleic acid delivery, comprising (a) contacting a nucleic acid with a polylinker, wherein the nucleic acid complexes with the polylinker to form a nucleic acid-polylinker complex, and (b) immobilizing the nucleic acid-polylinker complex of step (a) to a support substrate able to support cell adhesion, wherein the immobilization is through the polylinker, and wherein delivery of the nucleic acid to a cell is controlled by (i) density and location of the complex on the surface of the support substrate, and (ii) the number of bonds attaching the polylinkers in the complex to the support substrate.

In specific embodiments, the complexes may be covalently or non-covalently immobilized through the polylinker to the support substrate. In one embodiment, the complexes are covalently attached to the support substrate. In another embodiment, the complexes are non-covalently immobilized to the support substrate. In either embodiment, the complexes may be formed by condensation of the nucleic acid with a modified polylinker, by condensation of the nucleic acid with a non-modified polylinker, or by condensation of the nucleic acid with a mixture of modified polylinker and non-modified polylinker. The number of bonds linking the polylinker to the support substrate can be manipulated by i) varying the extent of modification of the polylinker, or ii) varying the ratio of modified to non-modified polylinker during complex formation.

In one embodiment, the support substrate is modified with a functional group capable of interacting with the non-modified polylinker in the complex. In another embodiment, the polylinkers are modified with a first functional group prior to step (a) and the support substrate is modified with a second functional group capable of interacting with the first functional group. In one embodiment, the nucleic acid is contacted with both modified and unmodified polylinkers, forming nucleic acid-polylinker complexes which bind to the support substrate with varying binding strengths, and thus are released over a period of time as a result of the different bond strengths. In another embodiment, the bond between the polylinker and the support substrate is reversible. In a further embodiment, the support substrate may be modified with a second functional group able to interact with the first functional group modifying a polylinker. In a specific embodiment, polylinker is poly-L-lysine (PLL), the first functional group is biotin, and the second functional group is avidin, strepavidin, or an avidin derivative.

In a third aspect, the invention features a method of making a controlled nucleic acid delivery system, comprising (a) contacting a nucleic acid with polylinkers; wherein the nucleic acid complexes with the polylinkers to form a condensed nucleic acid; and (b) immobilizing the polylinker present in the complex to a support substrate, wherein delivery of the nucleic acid to a cell is controlled by (i) density and location of the complex on the surface of the support substrate, and (ii) reversibility of the attachment of the polylinker to the support substrate the number of bonds linking the polylinker in the complex to the support substrate wherein a desired release rate is achieved. In one embodiment, the polylinkers are modified with a first functional group prior to step (a) and the support substrate is modified with a second functional group capable of interacting with the first functional group. In a further embodiment, the nucleic acid is contacted with both modified and unmodified polylinkers.

In a fourth aspect, the invention features a method of spatially controlling the delivery of a nucleic acid to a cell comprising: (a) modifying a polylinker with a first functional group; (b) contacting a nucleic acid with modified polylinker; wherein the nucleic acid complexes with the polylinker to form a condensed nucleic acid; and (c) immobilizing the nucleic acid-polylinker complex to a surface of a support substrate, wherein the surface of the support substrate is modified with a second functional group capable of interacting with the first functional group, and wherein complexes formed with modified polylinker are specifically bound to the support surface, and wherein the specific binding of the complexes to the surface of the support substrate is located at specific regions of the substrate in a defined pattern.

In one embodiment, the nucleic acid is contacted with both modified and unmodified polylinker in step (a) and the unmodified polylinker in the complex is not bound to the support surface in step (c). In a specific embodiment, the substrate is a microtiter plate comprising multiple wells.

In a fifth aspect, the invention features a method of temporally controlling the delivery of a nucleic acid to a cell population comprising: (a) modifying a polylinker with a first functional group; (b) contacting a nucleic acid with modified polylinker; wherein the nucleic acid complexes with the polylinker to form a condensed nucleic acid; and (c) immobilizing the nucleic acid-polylinker complex to a surface of a support substrate, wherein the surface of the support substrate is modified with a second functional group capable of interacting with the first functional group, and wherein the modified polylinker present in the complex is specifically bound to the support surface, and wherein the specifically bound complexes are released at desired times and internalized by a cell adhering to the surface of the support substrate.

In a sixth aspect, the invention features a method of temporally and spatially controlling the delivery of a nucleic acid to a cell population comprising: (a) modifying a polylinker with a first functional group; (b) contacting a nucleic acid with modified polylinker; wherein the nucleic acid complexes with the polylinker to form a condensed nucleic acid; and (c) immobilizing the nucleic acid-polylinker complex to a surface of a support substrate, wherein the surface of the support substrate is modified with a second functional group capable of interacting with the first functional group, and wherein complexes formed with modified polylinker are specifically bound to the support surface and located at specific regions of the substrate in a defined pattern, and wherein the specifically bound complexes are released at desired times and internalized by a cell adhering to the surface of the support substrate.

Other objects and advantages will become apparent from a review of the ensuing detailed description taken in conjunction with the following illustrative drawings.

DETAILED DESCRIPTION OF THE INVENTION

Figure 1:
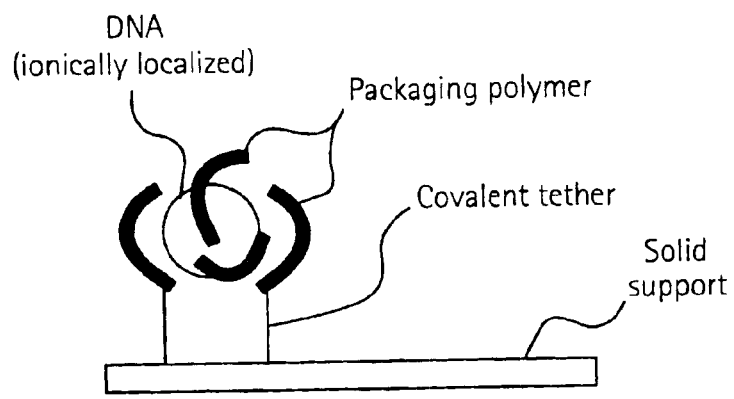
FIG. 1 is a schematic depiction of DNA condensation (ionically localized) with polymeric delivery to tether DNA complexes to the surface of a hydrogel.

Before the present methods and compositions are described, it is to be understood that this invention is not limited to particular methods, compositions, and experimental conditions described, as such methods and compounds may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a polylinker" includes mixtures of such polylinkers, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Definitions

By the term "nucleic acid", "gene", or the like, is meant a polynucleotide such as a plasmid, DNA, or RNA capable of being internalized by a cell in the nucleic acid-polylinker complex of the invention. The internalized nucleic acid may encode a protein, a growth factor, a hormone, etc., or may be an antisense oligonucleotide which interferes with the expression of a gene. The instant invention provides a condensed nucleic acid in the form of a nucleic acid-polylinker complex immobilized on the surface of a support substrate; the complex is released from the surface of the support substrate into the cell microenvironment, and is capable of being internalized by the cell. As shown in the experiments reported below, a cell taking up the released complex is transformed and able to express the transgene of the internalized complex.

The terms "support substrate", "solid substrate", "solid support", "support" and "supporting scaffold" are used interchangeably and represent a material that binds a polylinker which is complexed with a nucleic acid, which provides a surface for a cell to interact with the nucleic acid associated with the solid substrate, and which is biocompatible, e.g., non-toxic, to cells.

The solid substrate either contains, or can be chemically modified to contain a functional group that allows the solid substrate to covalently bind to a bifunctional polylinker. Examples of material that can be used as solid substrates include glass, peptide polymers (e.g., collagen), peptoid polymers, polysaccharides (including commercial beads, e.g., SEPHADEX and the like), carbohydrates, hydrophobic polymers, polymers, tissue culture polystyrene, planar lipid layers, planar lipid bilayers, metals, derivatized plastic films, glass beads, plastic beads, alumina gels, magnetic beads, nitrocellulose, cellulose, nylon membranes, cotton, and glass wool.

Figure 5:
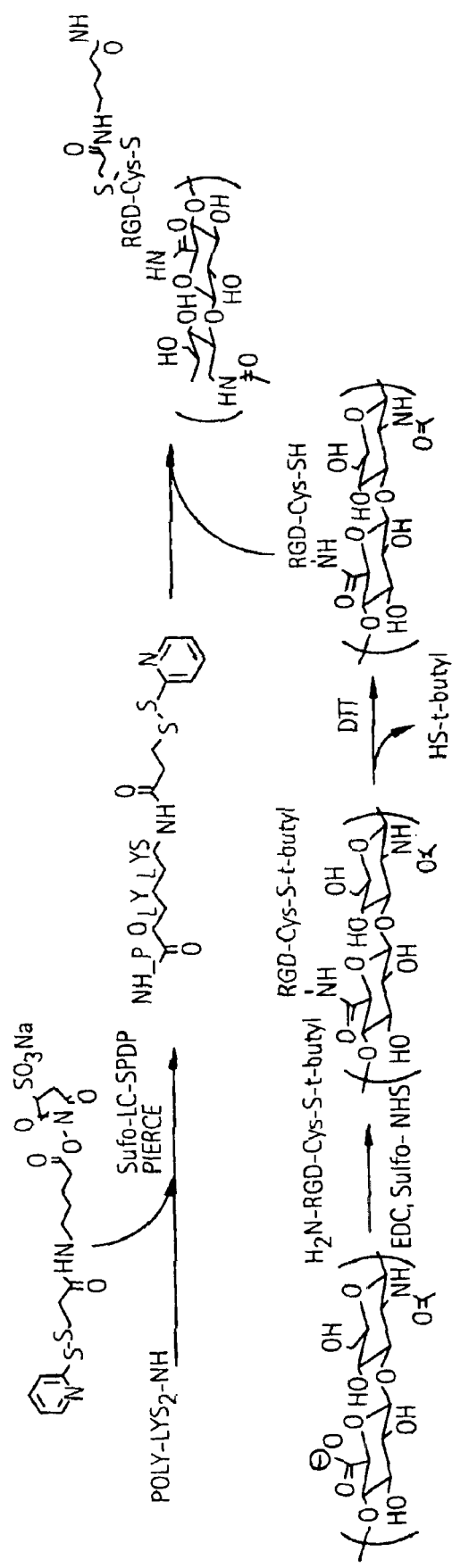
FIG. 5 depicts a method of surface modification and DNA tethering.
Figure 6:
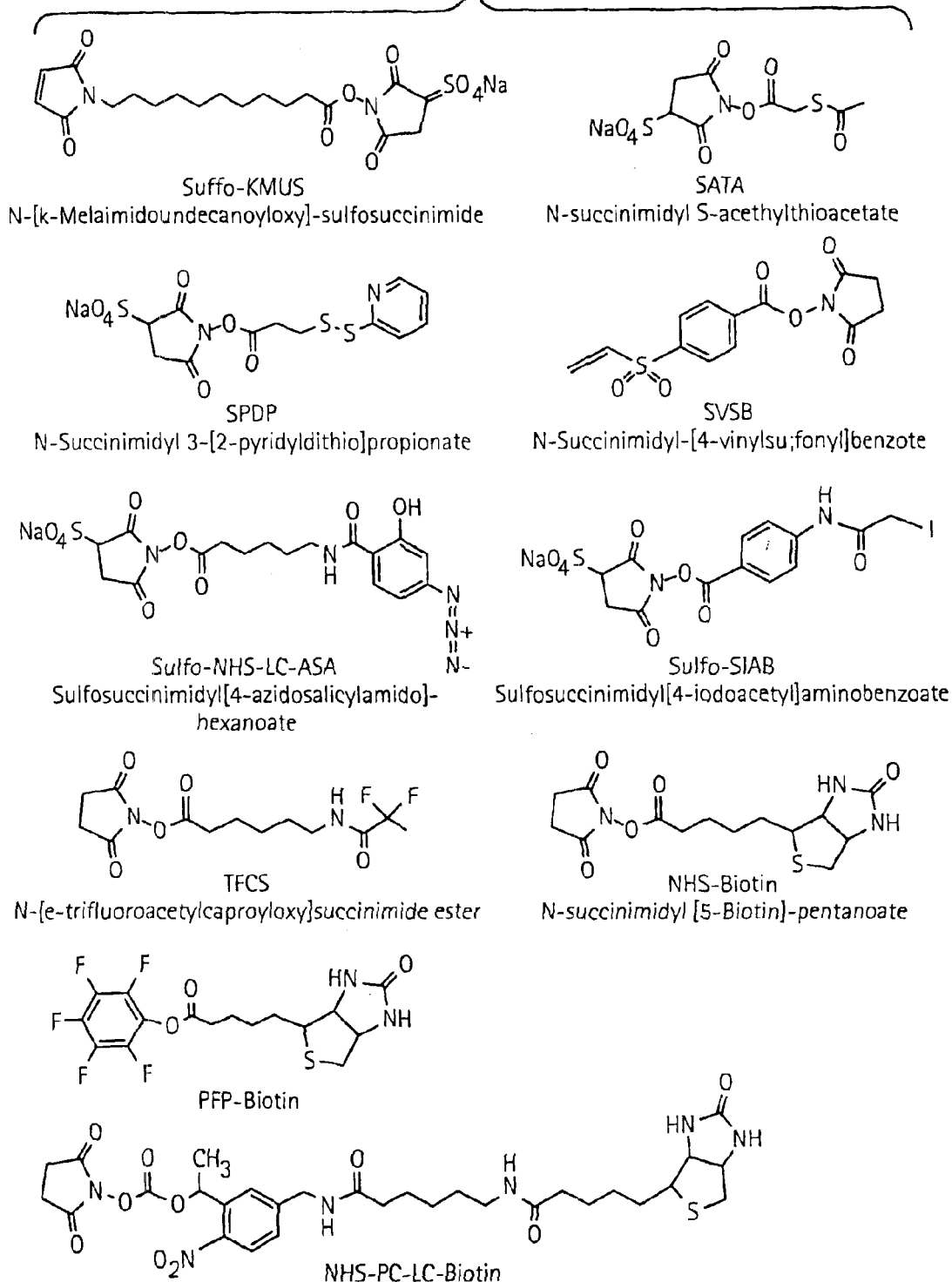
FIG. 6 shows the chemical structures of bifunctional cross-linkers exemplifying some of the types of compound that can be employed by the present invention. These cross-linkers are bifunctional, e.g., having two reactive centers. As shown, these molecules have their reactive centers at opposite ends and can be used to bind two molecules together.

The term "bifunctional agent" is used interchangeably with "bifunctional cross-linker" and is a compound that comprises two chemically reactive groups such as a thiol, an amine, a ketone, or an aldehyde, or a pair of binding partners such biotin-streptavidin, biotin-avidin, antibody-antigen, and receptor-ligand. Particular bifunctional cross-linkers are exemplified in FIG. 6. Bifunctional cross-linkers are used in the present invention in one embodiment to covalently bind a polylinker to a support substrate, in which one end of the bifunctional cross-linker is covalently attached to a reactive group on the substrate and the other end is covalently bound to the polylinker. See FIG. 5 as an example of modification of the surface support and DNA tethering or immobilization.

The terms "polylinker" or "accessor molecule", are used herein inerchangeably to define a polymer or other cationic compound that can act to complex with and condense the molecule of interest, e.g., a nucleic acid, and immobilize it on or tether it to a solid substrate. Examples of polylinkers include cationic polymers, cationic peptides, cationic peptoids, or cationic compounds such as cationic lipids.

As used herein a "tether" is a bond that covalently or non-covalently attaches an accessory molecule to the solid substrate, either directly or through a bifunctional cross-linker. Preferably, this bond is reversible and/or can be broken enzymatically.

As used herein the term "condensed nucleic acid" is a nucleic acid (e.g., a DNA plasmid or an oligonucleotide) that is non-covalently associated with accessory molecules thereby forming a complex (see examples below). Examples of condensing agents include cationic polymers, cationic lipids and polycations.

As used herein the term a "molecule of interest" is a molecule that is tethered to a solid support for use in the methodology disclosed by the present invention. Such molecules of interest include nucleic acids such as aDNA (preferably a plasmid), an oligonucleotide, or a modified oligonucleotide (e.g., phosphorothioate).

General Description

The invention involves a nucleic acid-polylinker complex immobilized or tethered to a supporting substrate or scaffold, wherein a cell adhered onto the supporting substrate is capable of internalizing the nucleic acid complex and expressing the protein encoded by the nucleic acid.

The approach involves forming a non-covalent binding complex between the nucleic acid and the polylinker molecule. The polylinker molecules are bound to the solid substrate. The tethering of the complex serves to localize the nucleic acid to the surface, thus placing it directly into the cell microenvironment.

Nucleic Acids

The present invention therefore utilizes condensed nucleic acids in a complex with polylinkers, wherein the polylinkers or a percentage thereof, are covalently and/or non-covalently bound to the surface of the support substrate. In one such embodiment the nucleic acid is a DNA molecule. In a more specific embodiment, the DNA molecule is a plasmid. In a related embodiment the DNA molecule encodes a protein. In another embodiment the nucleic acid is an oligonucleotide, and in specific embodiments, the oligonucleotide is an antisense molecule, a ribozyme, or a triple helix molecule.

Antisense, Ribozymes, and Triple Helix Molecules

The antisense nucleic acids of the invention comprise a sequence complementary to at least a portion of an RNA transcript of a gene, however, absolute complementarity, although preferred, is not required. A sequence "complementary to at least a portion of an RNA," as referred to herein, means a sequence having sufficient complementarity to be able to hybridize under stringent conditions (e.g., highly stringent conditions comprising hybridization in 7% sodium dodecyl sulfate (SDS), 1 mM EDTA at 65° C. and washing in 0.1×SSC/0.1% SDS at 68° C., or moderately stringent conditions comprising washing in 0.2×SSC/0.1% SDS at 42° C. with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In another embodiment, the nucleic acid of interest is a ribozyme or triple helix molecule used to modulate the activity, expression or synthesis of the gene present in the cell. Techniques for the production and use of such molecules are well known to those of skill in the art.

Ribozyme molecules designed to catalytically cleave gene mRNA transcripts can be used to prevent translation of target gene mRNA and, therefore, expression of the gene product. (See, e.g., PCT International Publication WO90/11364, published Oct. 4, 1990; Sarver et al. (1990) Science 247:1222–1225).

Ribozymes are enzymatic RNA molecules capable of catalyzing the specific cleavage of RNA. (For a review, see Rossi (1994) Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see e.g., U.S. Pat. No. 5,093,246, which is incorporated herein by reference in its entirety.

While ribozymes that cleave mRNA at site specific recognition sequences can be used to destroy mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers (1995) Molecular Biology and Biotechnology: A Comprehensive Desk Reference, VCH Publishers, New York, (see especially FIG. 4, page 833) and in Haseloff and Gerlach (1988) Nature, 334, 585–591, each of which is incorporated herein by reference in its entirety.

Preferably the ribozyme is engineered so that the cleavage recognition site is located near the 5' end of the mRNA to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al. (1984) Science, 224, 574–578; Zaug and Cech (1986) Science, 231, 470–475; Zaug, et al. (1986) Nature, 324, 429–433; published International patent application No. WO 88/04300 by University Patents Inc.; Been and Cech (1986) Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the gene of interest.

As in the antisense approach, the ribozymes can be composed of modified oligonucleotides (e.g., for improved stability, targeting, etc.) and should be delivered to cells that express the gene of interest in vivo. A preferred nucleic acid for delivery involves using a DNA construct "encoding" the ribozyme under the control of a strong constitutive pol III or pol II promoter, so that transfected cells will produce sufficient quantities of the ribozyme to destroy endogenous mRNA encoding the protein of interest and inhibit translation. Because ribozymes, unlike antisense molecules, are catalytic, a lower intracellular concentration is required for efficacy.

Alternatively, the endogenous expression of an encoding gene of interest can be reduced by targeting deoxyribonucleotide sequences complementary to the regulatory region of the gene (i.e., the gene promoter and/or enhancers) to form triple helical structures that prevent transcription of the encoding gene of interest (See generally, Helene (1991) Anticancer Drug Des. 6(6), 569–584; Helene et al. (1992) Ann. N.Y. Acad. Sci., 660, 27–36; and Maher (1992) Bioassays 14(12), 807–815).

Nucleic acid molecules to be used in triplex helix formation for the inhibition of transcription in the present invention should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Antisense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Bifunctional Cross-linkers

In one method of the invention, bifunctional cross-linkers are used as first and second functional groups to immobilize the nucleic acid-polylinker complex to the surface of the support substrate. Bifunctional cross-linkers have two reactive centers, which are generally at opposite ends of the cross-linker, e.g., a first and a second functional group, and are used to bind two molecules together (see, for example, FIG. 2). Sulfo-KMUS, SPDP, SATA, SVSB, and Sulfo-SIAB react with primary amines at one reactive center and sulfhydryl groups at the other reactive center. Sulfo-NHS-LC-ASA contains two reactive centers that react with primary amines. The reactions at either end of this cross-linker are independent since the reaction involving the azidosalicylamido group is activated by ultraviolet light. TFC reacts with primary amino groups at one of its reactive centers and activated carboxylic acids at its other reactive center. NHS-biotin, PFP-Biotin, and NHS-PC-LC-Biotin only have one reactive center that reacts with amino groups, whereas, the natural binding of biotin to streptavidin is employed as the second reactive center. NHS-PC-LC-Biotin is unique because when it is exposed to ultraviolet light it releases the original primary amine containing the molecule.

Polylinkers

A polylinker is selected for condensing with the molecule of interest, e.g., a nucleic acid. In different embodiments, the polylinker is a cationic polymer, a cationic protein or peptide, or a cationic lipid. The polylinkers of the present invention function to form a complex with the molecule of interest, and to immobilize the complex to the surface of the support substrate. The polylinker may be covalently bound to the solid substrate. In a particular embodiment, the percentage of polylinkers covalently bound to the surface of the solid substrate is greater than 0.2%. In another embodiment, between 0.5–50% of the polylinkers are covalently bound to the surface of the solid substrate. In a more specific embodiment, between 1.0–25% of the polylinkers are covalently bound to the surface of the solid substrate. In a particular embodiment, the covalent bond between the polylinker and the solid substrate is broken after a cell is plated on the solid substrate.

Cationic lipids: The main components of a cationic lipid are a hydrophilic lipid anchor, a linker group, and a positively charged headgroup. The lipid anchor is typically either a fatty chain (e.g., derived from oleic or myristic acid) or a cholesterol group, which determines the physical properties of the lipid bilayer, such as flexibility and the rate of lipid exchange. The linker group is an important determinant of the chemical stability, bio-degradability, and transfection efficiency of the cationic lipid. Biodegradable lipids can be metabolized by various enzymes (e.g., esterases, peptidases) to minimize any toxicity. The linker can also provide sites for the introduction of novel side chains to enhance targeting, uptake, and trafficking. The positively charged head group on the cationic lipid is responsible for interacting with the negatively charged DNA and is a critical determinant of the transfection and cytotoxicity of liposome formulations. The headgroups differ markedly in structure and may be single- or multiple-charged as primary, secondary, tertiary, and/or quaternary amines. The hydrophobicity of the lipid moiety has a crucial effect on in vitro gene transfer. Multivalent headgroups, such as spermine, in a "T-shape" configuration tend to be more effective than their monovalent counterparts at facilitating gene transfer. Generally, increases in the linker length correspond to increases in the gene delivery activity. Mixing of DNA and cationic lipid results in the collapse of DNA to form a condensed structure—termed lipoplex—in which nucleic acids are buried within the lipid. The thermodynamic driving force for association of the DNA and lipid is the entropy increase from the release of counter ions and bound water associated with DNA and the lipid surface.

The colloidal properties (e.g., size, stability) of the lipoplexes are principally determined by the cationic lipid/DNA charge ratio and not the composition of the lipid or the helper lipid. The charge ratio (+/−) is typically defined as the number of amines on the cationic lipid relative to the number of phosphate groups on the DNA. A neutral charge ratio (1:1 charge ratio for lipid:DNA) should generally be avoided because it results in the formation of large aggregates (>1 $\mu$M). Lipoplexes prepared at a positive charge ratio and a negative charge ratio likely represent structures with different lipid and DNA packaging (Xu et al. (1999) Biophys. J. 77:341–353). At a positive charge ratio, large multilamellar vesicles (LMV, diameter 300–700 nm) transfect cells more efficiently than the small unilamellar vesicles (SUV, diameter 50–200 nm) (Felgner et al. (1994) J. Biol. Chem. 269:2550–2561; Turek et al. (2000) J. Gene Med. 2:32–40; Ross and Hui (1999) Gene Ther. 6:651–659). The order in which DNA and lipid are mixed is critical and significantly affects the lipid and DNA packing (Xu et al. (1999) supra). For the addition of DNA to lipid, a gradual increase in size is observed. When adding lipid to DNA, the particle size remains roughly constant until the amount of lipid positive charge exceeds the nucleic acid negative charge, whereupon the particles grow rapidly in size (Kennedy et al. (2000) Biophys. J. 78:1620–1633).

The net charge on the lipoplex affects its interactions with other components present in vivo and in vitro (e.g., media, serum, extracellular matrix glycoproteins, mucosal secretions), which can limit the transfection efficiency. A positive charge ratio, which facilitates interactions with the cell membrane, is generally preferred for in vitro studies (3:1), whereas in vivo use may require the charge ratio to be altered because of interactions with components of the physiological environment. The charge ratio of the complex determines the zeta potential, which ranges from −55 mV to +55 mV as the charge ratio is increased. Multivalent anions present in the serum or media can facilitate fusion of the lipids causing an increase in the size of the particle. Polyanions with adequate anionic charge density (e.g. heparin) released DNA from the complex by binding the cationic lipid. Serum can be a complicating factor for positively charged complexes, possibly causing premature release of the DNA from the complex and enhancing degradation by nucleases. For ON:lipid complexes, the various components of serum (e.g., BSA, lipoproteins, and macroglobulin) interact with the complexes and alter the complex diameter, zeta potential, and interfere with cellular uptake and nuclear trafficking.

To improve lipoplex stability, PEG-PE can be incorporated into the cationic liposome. Such liposomes are prevented from aggregating and interacting with serum components, which increases their stability (Hong et al. (1997) FEBS Lett. 400:233–237; Meyer et al. (1998) J. Biol. Chem. 273:15621–15627). Alternatively, a detergent can be placed in solution with the cationic lipid and DNA (Hofland et al. (1996) Proc. Natl. Acad. Sci. USA 93:7305–7309). Removal of the detergent by dialysis allows the formation of uniform complexes. Lyophilization can also increase their shelf life. Cryoprotectants (e.g., sucrose, trehalose) also can be added to prevent aggregation and fusion of plasmid/lipid complexes during lyophilization.

Formulations of cationic lipids have been widely applied for in vitro nucleic acid transfection (see, for example, Felgner et al. (1987) Proc. Natl. Acad. Sci. USA 84:7413–7417) and more than 30 products are commercially available for this purpose, including Lipofectin (a 1:1 mixture of DOTMA and DOPE), Transfectam, Lipofectase, Lipofect-AMINE, and LipoTaxi. Formulations of cationic lipids can further contain a zwitterionic or neutral colipid, such as DOPE or cholesterol, to enhance transfection.

Cationic Polymers: All cationic polymers contain high densities of primary amines, which are protonatable at neutral pH. This high density of positive charges allows the cationic polymers to form stable complexes with non-viral DNA. The cationic polymers self-assemble with DNA to generate condensed structures (40–100 nm in diameter) capable of entering the cell. Cationic polymers include polyallylamine, peptoids, methacrylamide, and cyclodextrin containing polymers. Such polymers vary widely in their structure, which ranges from linear to highly branched molecules and influences their complexation with nucleic acids and their transfection efficiency. In addition to providing positive charges for DNA complexation, the primary amines also serve as functional groups with which to chemically modify the polymers with ligands and peptides that can enhance one or more of the steps in the trasfection process.

Poly-L-lysine (PLL) and poly-L-ornithine are the most commonly used cationic polymers for gene delivery. Differing in chemical structure only by the length of their side chain (4 versus 3 carbons), they are capable of mediating gene delivery both in vitro and in vivo (Duguid et al. (1998) Biophys. J. 74:2802–2814). In order to form uniform complexes, these polymers are generally synthesized on a solid support using a series of protecting/de-protecting synthetic steps (e.g. Fmoc chemistry) to obtain mono-disperse peptides. PLL is typically used at charge ratios (+/−) ranging from 3:1 to 6:1. The ideal length of the PLL represents a balance between two competing effects: effective condensation and cytotoxicity. Relative to low molecular weight, the high molecular weight PLL forms tighter, smaller condensates that are more resistant to the effects of salt concentration and sonication [Adami et al. (1998) J. Pharm. Sci. 87: 678–683). However, cytotoxicity has been found to be inversely related to particle size (Duguid et al. (1998) supra), likely due to the high molecular weight PLL.

Poly(ethylenimine) (PEI) has been widely used to mediate gene delivery due to its high cationic charge density resulting from the protonatable amine on every third carbon. PEI can be synthesized by the acid catalyzed ring opening polymerization of aziridine as either a linear or a branched structure. Similar to the PLL complexes, low molecular weight PEI is less cytotoxic than high molecular weight PEI. Furthermore, PEI/DNA complexes must also bear a net positive charge (6–13:1+/–ratio) in order to efficiently transfect cells (Boussif et al. (1995) Proc. Natl. Acad. Sci. USA 92:7297–7301; Fischer et al. (1999) Pharm. Res. 16:1273–1279, Goula et al. (1998) Gene Ther. 5:712–717). The presence of sodium chloride during complexation can result in particles with amorphous shapes and diameters greater than 1 $\mu$m.

Dendrimers are an attractive architecture for gene transfer because their well-defined structure and robust chemistry enables the synthesis of many generations of protonatable amines. Starbust dendrimers such as polyamidoamine dendrimers (PAMAM) are capable of mediating gene delivery (Fischer et al. (1999) supra; Bielinska et al. (1997) Biochim. Biophys. Acta 1353:180–190; Qin et al. (1998) supra). PAMAM can be synthesized from either an ammonia or ethylenediamine core by successive addition of methyl acrylate and ethylenediamine (Tomalia et al. (1990) Angew Chem. Int. Ed. Engl. 29:138–175). The surface charge and diameter of the dendrimer is determined by the number of synthetic steps (i.e. number of generations). The generation of PAMAM used to complex DNA determines particle size and transfection efficiency. At charge ratios (+/−) above or equal to one, no free DNA is observed. Higher levels of transfection are observed for PAMAM/DNA complexes formed from generation 5 and 6 dendrimers than with lower PAMAM generations [Fischer et al. (1999) supra).

Cationic polymers can also be used in combination with liposomes. DNA is initially complexed with PLL at low charge ratios and cationic lipids are subsequently added to completely condense the DNA. Alternatively, the PLL condensed DNA containing a net positive charge can subsequently be complexed with an anionic lipid. Precondensation with polylysine has been shown to reduce serum inhibition and also enhanced the transfection efficiency (Vitiello et al. (1996), Gene Ther. 3:396–404; Gao and Huang (1996) Biochemistry 35:1027–1036).

Control of DNA Delivery to Cell

The nucleic acid may be internalized directly from the surface since each nucleic acid molecule is complexed with many acessory molecules and only a fraction of them are tethered. Alternatively, the tethers linking the complex to the surface may be broken, thus releasing the entire complex as a soluble factor into the immediate cellular microenvironment for internalization. This system also provides the potential to spatially and temporally control gene delivery to cells on the scaffold. Spatial control is obtained through regulating the location where the DNA is tethered to the surface. Temporal control is obtained through the number of tethers used in localizing the DNA complex to the surface. Release of the complex into solution or uptake by cells may not occur if few tethers remain; thus, the timing of release or uptake can be regulated through the number of tethers that must be broken. The surface density of DNA, the number and type of tethers, the properties of the scaffold, and the design of the polylinker are major design criteria that affect release and uptake.

The number of tethers can be used to regulate how tightly a molecule of interest is associated with the solid support. Fewer tethers can allow for a quicker release or uptake of the molecule of interest, whereas more tethers can delay the release or increase uptake time.

The tethers or the bifunctional cross-linkers of the present invention can either be transient, that is a tether that they can be designed to break or be broken after a certain desired time frame, or they can be designed to be relatively stable, such as a protein which is susceptible to proteolytic enzymes, or alternatively, the tether can be relatively stable such a plastic or nylon.

In the case of a transient tether, the freeing of the molecule of interest can be effected by hydrolysis, in which the tether degrades slowly with time in the presence of water. In another embodiment, the tether is sensitive to an outside stimulus such as light, free radicals, radiation, etc., thereby being degraded by the stimulus and releasing the molecule of interest. One example of a transient cross-linker, is a protein that can be enzymatically cleaved causing the molecule of interest to be released. The enzymes catalyzing the bond-breaking reaction may be secreted by the cells or alternatively may be present in the extracellular space.

In the case of a permanent tether or cross-linker, the molecule of interest would not be released as a soluble factor into the media, but would have to interact with the cell directly from the substrate surface. If the molecule of interest needs to be internalized, the cell would have to pull the molecule away from the components that link it to the surface; thus, the strength of interaction of the molecule with the cell would need to be greater than the interaction of the molecule with the substrate. Alternatively, the solid substrate itself may degrade to release the molecule of interest.

In one particular aspect, the method of the present invention spatially controls gene delivery to cells within predefined domains on a support substrate. A DNA sequence encoding for a specific gene, for example, is localized to a distinct domain on a support (e.g., a glass slide) for delivery to cells cultured within that domain. Internalized of the DNA complex modulates the expression of a specific gene within each domain. Thus, an array of cells is created in which gene expression varies between domains.

Reporter genes can be used to quantify the effectiveness of gene delivery. Reporter genes enable the quantification of the spatial location of protein production and the quantity of protein produced. A plasmid encoding for green fluorescent protein (GFP) for example, may be used to follow expression in the cell population cultured on the surface over time using a fluorescence microscope (see the examples below). The quantity of protein production also can be quantified using the reporter gene luciferase, which is assayed with a luminometer.

Uptake of the complex can be tracked by attaching a label (e.g., a fluorescent tag) to the molecule of interest or to the tether polylinker. The labeled molecule could be followed by fluorescence microscopy to determine if it has been internalized or acted upon by the cell. Labeling the tether polylinker with one fluorescent tag and the molecule of interest with a different tag may be used to follow the position and timing of each component separately.

The technique of tethering DNA to adhesive surfaces for enhanced gene transfer has additional applications for in vivo gene delivery and tissue engineering. Tethering of DNA to the surface of a solid support (e.g., polymer, glass)

increases cellular uptake by placing the DNA directly at the cell surface, thus overcoming many mass transfer limitations associated with gene transfer. Cells will adhere to the material surface to which the DNA is tethered. Additionally, the tethering provides for a technique to control which cells have access to the DNA and allows for spatially regulated gene delivery.

In the present invention, controlled gene delivery and expression is achieved by sequestering DNA to specific locations, using techniques that still allow for internalization and expression. The strategy, shown in FIG. 1, combines the techniques of protein patterning, DNA packaging, and sustained release. In one example of the method of the invention, plasmid DNA is initially complexed with multiple types of cationic peptides in a process known as DNA condensation—a process designed to enhance cellular uptake and nuclear trafficking. Hundreds of cationic peptides bind to each plasmid. A fraction of these peptides are subsequently tethered to a support substrate using techniques established for controlled protein delivery. A support substrate can be glass or plastic, but for in vivo gene delivery and tissue engineering is more preferably a biocompatible solid substrate such as collagen or alginate, or a polyethylene glycol (PEG) based hydrogel. The tethering results in DNA being localized ionically at the surface of the support substrate by the covalently bound peptides. The peptides function to package the DNA for efficient transfection while the substrate surface localization maintains the DNA in the cell microenvironment for extended times, thus providing prolonged opportunities for internalization. The optimal number of tethers represents a balance between competing effects. If no tethers are present, the DNA is free in solution to be internalized, but spatial control cannot be achieved. If every peptide is a tether, internalization may not be possible because of the strong ionic interaction between the DNA and the peptide. Therefore, the amount of tethering of the DNA to the support substrate will vary with application. This can be achieved by forming DNA complexes that are tethered to the solid support with varying number of tethers. For example, cells can be seeded onto the solid support and examined for their ability to internalize and express a given gene. The optimal number of tethers to employ is therefore, readily determined by testing this parameter for any given desired application.

Another consideration is that the number of tethers can be designed to decrease with time, either through the action of proteases or through a degradable linker. The appropriate tethering serves to maintain the DNA at the surface for internalization either by receptor-mediated endocytosis which pulls the DNA from its ionic interaction with the tether or by degradation of the tethers which releases the DNA complex into solution in the cell microenvironment.

Cell Culture

Cells seeded onto the solid substrate can be cultured in vitro to ultimately produce tissues or portions of tissues for tissue transplantation. The culturing of cells on the solid substrate can be performed by placing the cell/solid substrate in a medium that contains the necessary factors for cell survival. The cell/solid substrate is subsequently placed in a 37° C. incubator, that may have controlled humidity and oxygen tension. Frequently, culturing of cells is performed in a bioreactor which acts to tightly regulate the temperature, oxygen and nutrient supply for optimal cell growth on the solid substrate.

The present invention also provides methods for preparing tissue ex vivo. One such embodiment comprises seeding a cell on a solid substrate of the present invention and culturing the cell in a medium that contains the necessary factors for survival. In a particular embodiment the cell is a native progenitor cell. In another embodiment the cell is a transplanted stem cell. In a particular embodiment the cell is an osteoblast. In yet another embodiment, the cell is a hematopoietic stem cell. In still another embodiment, the cell is a hepatocyte. In yet another embodiment, the cell is an embryonic stem cell. In a particular embodiment the condensed nucleic acid of the solid substrate had been delivered in a spatially controlled pattern to the solid substrate. In a preferred embodiment, the condensed nucleic acid comprised by the solid substrate encodes a protein that directs tissue formation. In a particular embodiment of this type, the protein is a growth factor. In an alternative embodiment the protein is a cytokine. In still another embodiment, the condensed nucleic acid comprised by the solid substrate encodes a transcription factor. In yet another embodiment, the condensed nucleic acid comprised by the solid substrate encodes at least two of the following: a growth factor, a transcription factor and a cytokine.

Applications

Tissue engineering aims to create functional tissue replacements for patients suffering from organ loss or tissue failure. To achieve this objective, these tissues will develop from native progenitor cells or transplanted stem cells on a synthetic scaffold that mimics the natural environment. Controlled gene delivery allows spatial variations in gene expression enabling the organization of multiple cell types within a tissue (e.g., nerve cells surrounded by supporting Schwann cells) or provide a directional signal (e.g., neurite extension). Temporal patterns regulate the switching of cell function from an immature to a mature stage. For example, during bone development, osteoblasts switch from an initial proliferation stage to a final mineralization stage. By means of controlled gene delivery, tissues could be engineered by incorporation of appropriate signals into a support scaffold.

An application of spatially controlled gene delivery is nerve regeneration. Neurite extension is guided by gradients in various factors (e.g., NGF, netrins). Spatially controlled expression of these genes can be used to create these concentration gradients. The number and orientation of neurites in response to the chemical gradients are quantified as measures of the cellular response.

An application of temporally controlled gene delivery is bone development, which has been characterized by three stages. The expression of stage-specific genes is examined for effects on mineralized tissue formation. A gene encoding for a growth factor (e.g., TGFβ) is delivered early to increase cell density while a second gene (e.g., osteocalcin) is delivered later to enhance mineralization. Cell density, mineralization, and bone-specific gene expression are used as measures of tissue formation. These applications demonstrate the potential of this approach, which has additional application to numerous cell systems.

The present invention also provides methods of determining the effect of gene expression on cell function. A particular method of this type comprises adding a cell to a well of the microtiter plate comprising multiple wells in which the wells contain condensed nucleic acids encoding a protein. The function of the cell is then monitored. The effect of the expression of the protein encoded by the condensed nucleic acid on cell function is then determined. In another approach, the cells are then assayed for a desired effect, for example, decreased resistance to a chemotherapeutic drug. The DNA molecule encoding the protein causing the response can be identified based on its location in the array. Similar approaches could be used using arrays of antisense oligonucleotides; for example, by preparing DNA polylinker complexes with different DNAs of unknown function, tethering the complexes to a solid support in a microarray format, and adding cells to in an array, cells plated on the array would then be assayed for their ability to respond to certain stimuli. In this manner, one could identify important targets for pharmaceutical intervention (e. g., through the use of pharmaceutical compositions comprised of antisense oligonucleotides or other molecules inhibiting the expression or activity of the target). The invention also provides a useful tool for research; e. g., by selectively inhibiting the expression of different proteins involved in intracellular signaling, one could identify the signaling pathways involved in a cellular response to a stimulus. It is anticipated that the cell function assays of the present invention can be adapted into a format suitable for high-throughput screening.

The present invention further provides methods for regenerating tissue at the site of a wound. In one embodiment, the method comprises contacting a solid substrate of present invention with a cell at the site of the wound. In a preferred embodiment of this type, the condensed nucleic acid comprised by the solid substrate encodes a protein that directs tissue formation. In a particular embodiment of this type, the protein is a growth factor. In an alternative embodiment the protein is a cytokine. In still another embodiment, the condensed nucleic acid comprised by the solid substrate encodes a transcription factor. In yet another embodiment, the condensed nucleic acid comprised by the solid substrate encodes at least two of the following: a growth factor, a transcription factor and a cytokine.

Creating Spatial Patterns for Expression of the Nucleic Acid

Spatial patterning of genes onto surfaces can be performed using a multitude of methodologies. For example, an arrayer may be used to place a specified volume onto a specific spot on the solid substrate. An arrayer is currently being employed to spatially pattern oligonucleotides for gene chips. Alternatively, microfluidics technology can be used to specifically deposit a liquid containing DNA onto a specific region of the solid substrate. In yet another embodiment, the solid substrate can be chemically modified using any of a variety of photolithography techniques.

Specific Embodiments

Thus the present invention combines DNA condensation with polymeric delivery to tether DNA complexes to a surface (FIG. 1), to which cell adhesion can be controlled. DNA is ionically complexed with a cationic peptide to stabilize against degradation and to enhance uptake. A fraction of the cationic peptides that package the DNA are subsequently tethered to the surface of a support substrate, thus maintaining the DNA at the surface through an ionic interaction. The linkages can be designed to be temporary, either through enzymatic degradation of the bifunctional crosslinker or through a reversible tether. The mechanism of uptake may be direct internalization of the plasmid from the surface (e.g., few tethers per complex) or may follow complete degradation of the tethers or bifunctional crosslinkers, which would release the plasmid directly into the cell microenvironment. Controlled delivery and uptake occurs through variations in the type and number of tethers per plasmid.

Figure 2:
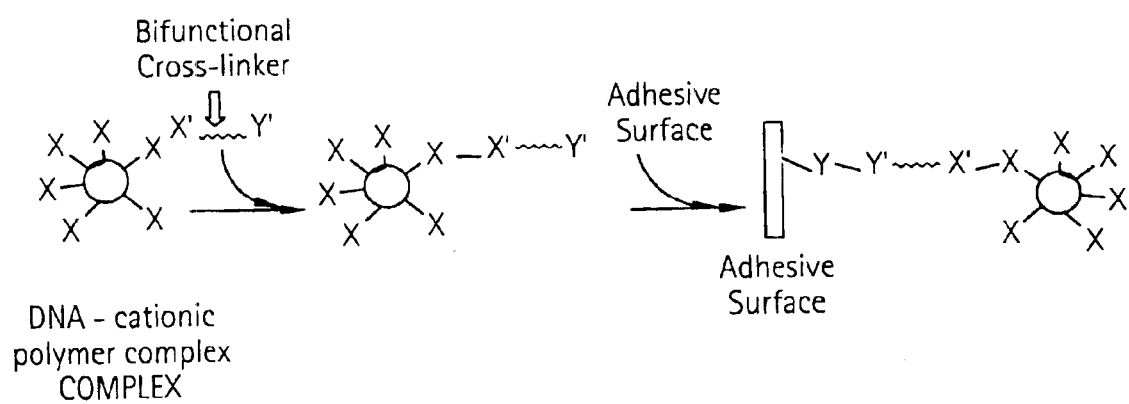
FIG. 2 is a schematic depiction of the coupling of DNA complexes to the surface with a bifunctional cross-linker.

One important aspect of the present invention is based upon the efficient and spatially controlled delivery of nucleic acids to cells cultured on a slide. By themselves, plasmid DNA and oligonucleotide are not efficiently internalized by cells and delivery cannot be spatially controlled; however, packaging the nucleic acids into complexes can overcome these limitations. Complexation with a cationic polymer (e.g., poly-L-lysine, PLL)—a process termed condensation—produces a particle with size ranging from 40–100 nm, a size readily internalized by cells (Mahato et al. (1999) Adv. Genet. 41:95–156). These condensates can contain fusogenic peptides or nuclear localization signals or may be functionalized with receptor ligands to enhance targeting, internalization, and intracellular trafficking of the complex (Cristiano and Curiel (1996) Cancer Gene Ther. 3:49–57). The desired spatial control over delivery is obtained by combining DNA complexation with spotting technology and localized drug delivery. Following condensation, plasmids and oligonucleotides are spotted into domains (100–500 $\mu$m) on a slide using, for example, the Affymetrix Pin and Ring. The nucleic acid condensate is retained within the domain by subsequent tethering of the complex to the surface using a bifunctional cross-linker (FIG. 2). One functional group on the cross-linker is coupled to a fraction of the cationic polymers that condense the nucleic acid. The remaining functional group on the bifunctional cross-linker reacts with functional groups on the surface, thus tethering the complex to the surface. The nucleic acid is maintained ionically at the surface for direct delivery into the cell microenvironment. Sustained plasmid delivery from surfaces that support cell adhesion has demonstrated an increased uptake and expression (Shea et al. (1999) supra), likely due to high concentrations at the cell surface (Luo et al. (2000) supra) and prolonged exposure to the plasmid, which provides multiple opportunities for internalization.

In a particular embodiment of the present invention a support surface is employed that has the ability to gel upon implantation into the body (Elisseeff et al. (1999) Plast Reconstr Surg, 104:1014–1022). Implantation of the material results in gelling and filling of the desired space. Cells from the surrounding tissue would then interact with the material and would be presented with the molecule of interest to direct its action, such as for regeneration of a tissue (i.e., tissue engineering), stimulation of an immune response (e.g., cancer therapies), secretion of a therapeutic molecule (i.e., during delivery), or any other desired cell function.

Example 1 below describes experiments examining tethering complexed polylysine (PLL)/DNA on glass slides, surface densities achieved, and use in cell transfection.

Figure 7:
FIG. 7 shows the results of HPLC analysis of the formation of biotinylated $K_{19}$, starting material 1 and the reaction mixture 2. The shift in molecular weight between 1 and 2 and absence of the low molecular weight peak in 2 confirmed that the reaction went to completion.
Figure 8:
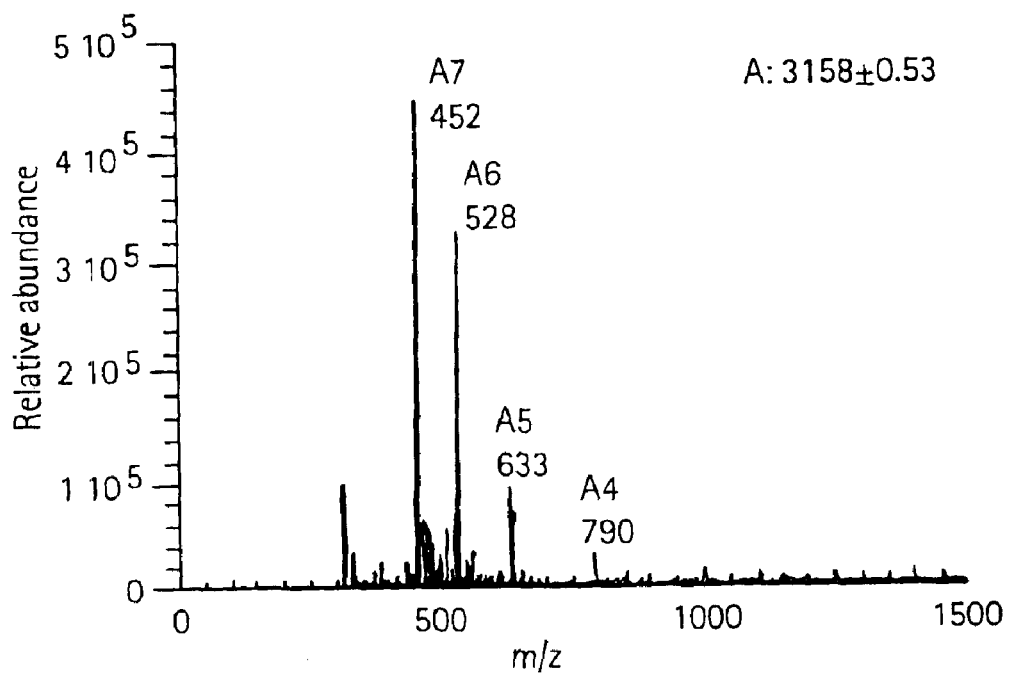
FIG. 8 shows the results of mass spectrometric analysis of the purified reaction mixture of the formation of biotinylated $K_{19}$.

Example 2 describes the synthesis of biotinylated PLL and complexation with DNA. Polylysine was covalently modified with biotin residues either through an N-terminal cysteine side chain ($K_{19}$) or through an amine ($K_{150}$). HPLC analysis of the initial peptide ($K_{19}$) and the peptide reaction mixture ($K_{19}$-B) demonstrated that the reaction proceeded to completion (FIG. 7), as evidenced by the increase in molecular weight in the reaction mixture and the absence of the lower molecular weight $K_{19}$ peak. Mass spectrometry (FIG. 8) suggests that the approach for modifying the peptide $K_{19}$ results in the attachment of a single biotin group. A good correspondence was found between the theoretically expected molecular weight for $K_{19}$ modified with a single biotin (3158 Da), and the experimentally obtained molecular weight (3157.66±0.77 Da). Alternatively, the chemistry employed for modification of $K_{150}$ allows for multiple biotin residues to be attached per PLL. The $K_{150}$-B synthesis resulted in a 3.1:1 molar ratio of biotin to $K_{150}$ by using a 10:1 molar ratio of biotinylation reagent to $K_{150}$ in the reaction mixture.

As described in Example 3, the synthesized biotinylated and non-biotinylated peptides were subsequently analyzed for their ability to complex with DNA using gel electrophoresis. The non-biotinylated peptides ($K_{19}$, $K_{150}$) completely eliminate the electrophoretic mobility at charge ratios of 3.1 and 1.2 respectively (results not shown). However, the presence of the biotin group on the peptide affected the charge ratio at which the mobility is eliminated, which is 4.6 and 4.9 for $K_{19}$-B and $K_{150}$-B respectively. Mixtures of $K_{150}$-B with $K_{19}$ were also examined by gel electrophoresis for DNA complexation at a charge ratio of 5.5:1. The inhibition of mobility was observed for all combinations of the two peptides. The results illustrate that the biotinylated peptides, non-biotinylated peptides, and mixtures of biotinylated and non-biotinylatd peptides are capable of electrostatically neutralizing plasmid DNA and eliminating its electrophoretic mobility.

The availability of the biotin groups on the PLL for tethering to a surface was determined using the affinity of biotin for neutravidin (non-glycosylated avidin). Surface-associated DNA was visualized for DNA complexed with $K_{150}$-B. Fluorescence images taken after the initial incubation on the surface and before the wash demonstrates the presence of complexes across the entire surface (results not shown). Thorough washing of the surfaces resulted in a reduction of the quantity of surface-associated DNA. All subsequent studies used surfaces that were thoroughly washed to ensure binding specificity of the complexes.

Figure 9:
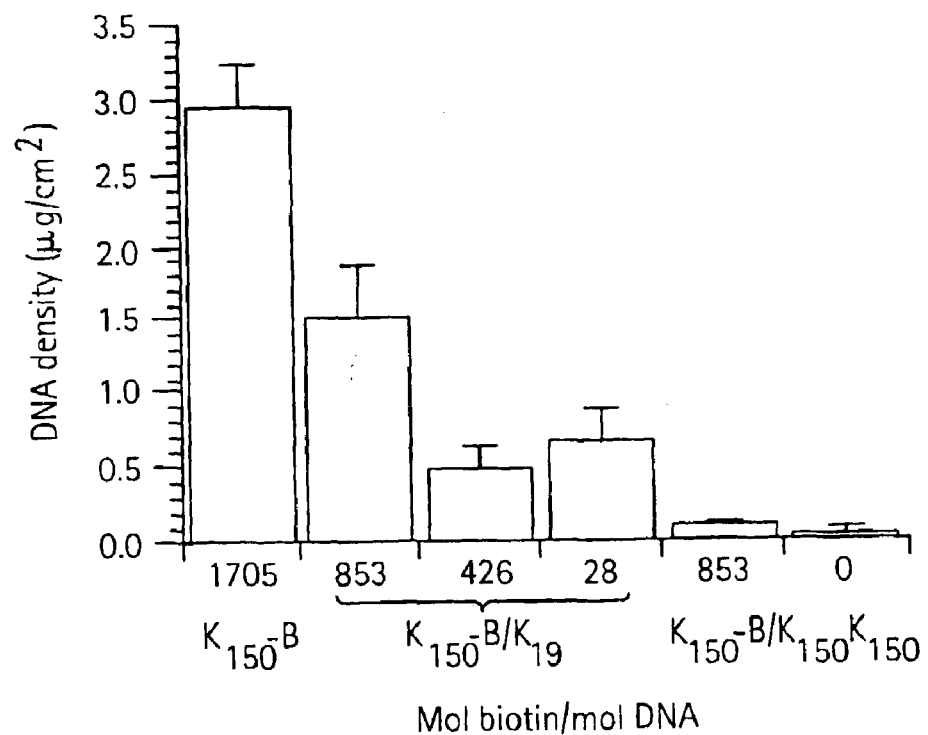
FIG. 9 shows the density of surface-associated DNA for complexes formed by mixing $K_{150}$-B DNA with either $K_{19}$ or $K_{150}$ at a charge ratio of 5.5. The moles of biotin per mole DNA (i.e., average number of biotin groups per complex), which varied from 28 to 1705 for $K_{150}$-B and 217 to 4342 for $K_{19}$-B, are listed beneath each bar. The symbol * indicates statistical significance ($p<0.05$) in the surface densities relative to complexes without biotin.
Figure 10:
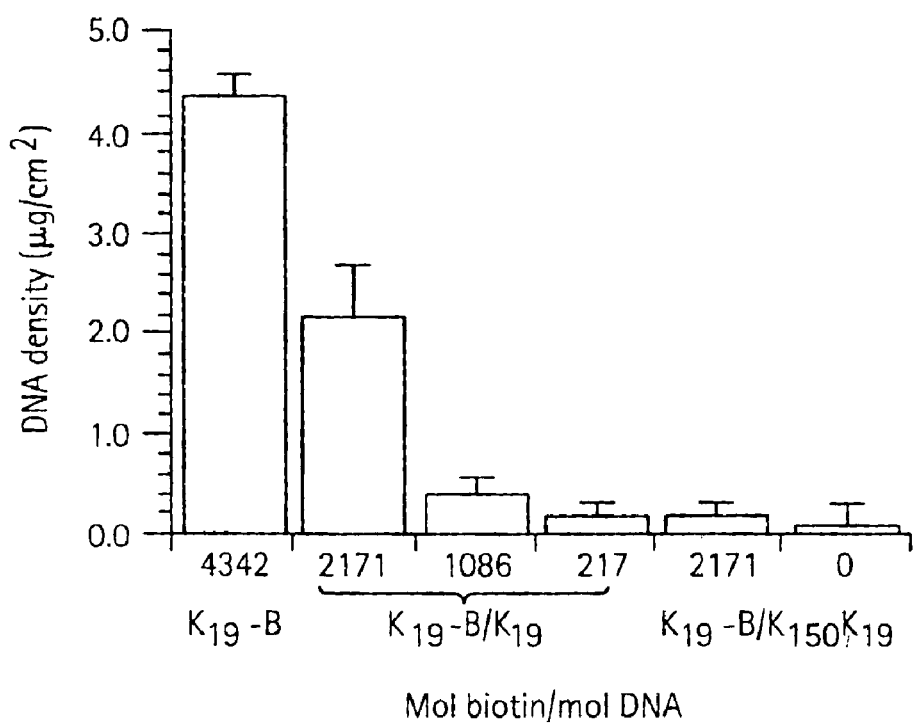
FIG. 10 shows the density of surface-associated DNA for complexes formed by mixing $K_{19}$-B DNA with $K_{150}$-B with either $K_{19}$ or $K_{150}$ at a charge ratio of 5.5 as described in FIG. 11.

The quantity of surface associated DNA was subsequently measured as a function of the PLL peptides and the number of biotin groups per complex. Non-biotinylated peptides used for DNA condensation resulted in low surface densities (<0.1 μg DNA/cm$^2$) due to non-specific adsorption. The use of biotinylated peptides for DNA complexation increased the surface density of DNA relative to the condition of no biotin groups (p<0.05), suggesting that biotin groups are available on the DNA complexes for interactions with the surface-associated neutravidin. The maximal amount of surface-associated DNA was observed for DNA complexes formed solely with biotinylated peptides (p<0.001), with densities of 2.9 and 4.3 μg DNA/cm$^2$ obtained for $K_{150}$-B and $K_{19}$-B respectively (FIGS. 9–10). Complexes formed from either $K_{150}$-B or $K_{19}$-B were calculated to have an average number of biotin groups equal to 1705 and 4342 respectively. These surface densities correspond to a tethering efficiency (mass DNA on surface/mass DNA added) of 24% ($K_{150}$) and 35% ($K_{19}$). For the $K_{150}$-B and $K_{19}$-B, decreasing the amount of DNA incubated on the surface was found to decrease the amount of surface-associated DNA (data not shown). The quantity of surface-associated DNA was also found to decrease as the number of biotin groups in the DNA/PLL complex decreased. The molecular weight of polylysine, both biotinylated and non-biotinylated also affected the quantity of surface-associated DNA. For the biotinylated peptide $K_{150}$-B, fewer numbers of biotin groups were required to obtain an equivalent amount of surface associated DNA as for the peptide $K_{19}$-B. However, the use of the non-biotinylated peptide $K_{19}$ for complexation resulted in increased DNA surface densities relative to the use of $K_{150}$.

Figure 11:
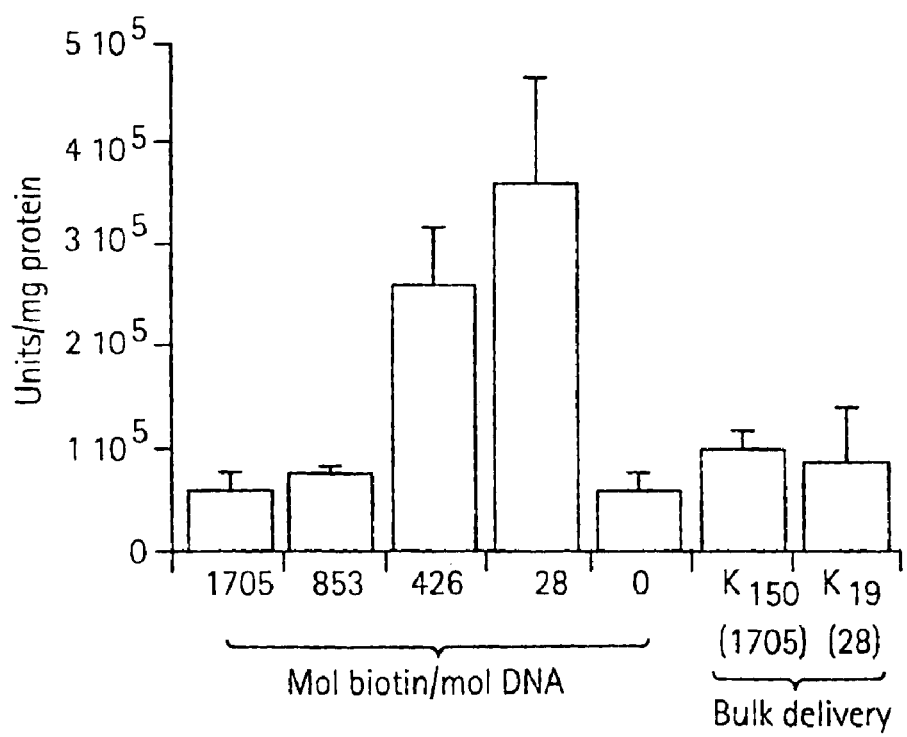
FIG. 11 shows the expression levels achieved by surface mediated transfection after 48 hours of incubation for HEK293T cells determined using an assay for β-galactosidase activity. The symbol * indicates statistical significance in transfection levels ($p<0.05$) relative to both bulk delivery conditions.
Figure 12:
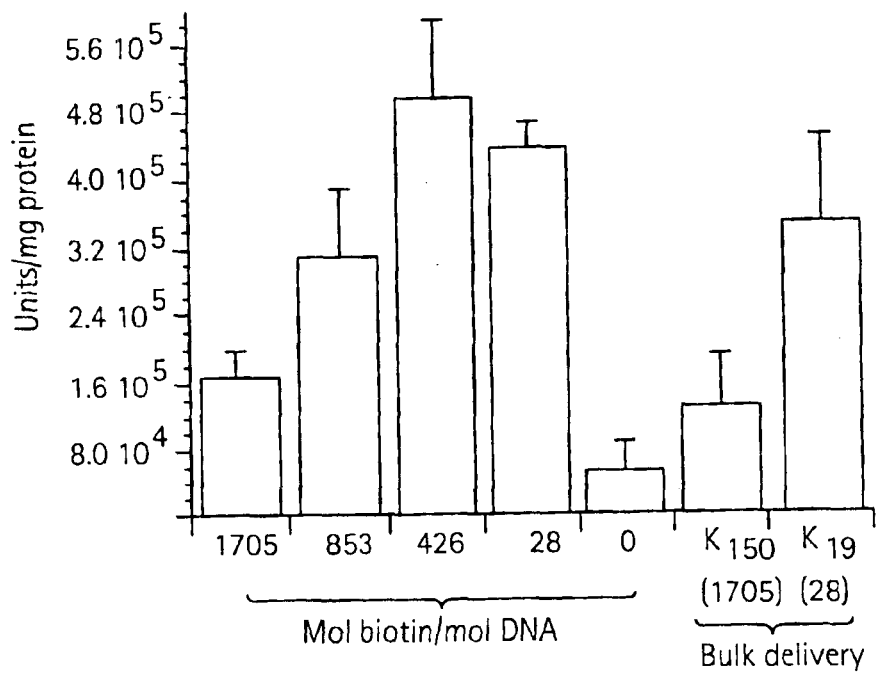
FIG. 12 shows the expression levels achieved by surface mediated transfection after 48 hours of incubation for NIH/3T3 cells as described in FIG. 11.

Culture of HEK293T and NIH/3T3 cells on the DNA modified surfaces led to cellular transfection at 48 hours, with levels of protein production equal to or greater than that obtained by bulk delivery. The transfection experiments (Example 4) used mixtures of $K_{150}$-B and $K_{19}$ for DNA complexation because this combination had an increased amount of surface associated DNA relative to the other peptide mixtures, particularly when the complexes had few numbers of biotin groups. Quantification of protein expression levels for HEK 293T demonstrated that complexes with 28 and 426 biotin groups produced the maximal transfection (FIG. 11), which was statistically greater (p<0.05) than other conditions with greater numbers of biotin groups. Expression levels obtained for surface-associated complexes with 1705 and 853 biotin groups were not significantly different from the control conditions, which consisted of bulk delivery of DNA complexes formed from either $K_{150}$ or $K_{19}$. For bulk delivery, the amount of DNA added in complexes with $K_{150}$ or $K_{19}$ corresponded to the surface quantities of DNA for $K_{150}$-B (1705 biotin groups) and $K_{150}$-B/$K_{19}$ (28 biotin groups), respectively. These conditions were chosen as the control conditions to represent the limiting cases of surface associated delivery regarding DNA quantities (0.7 μg and 0.16 μg) and PLL composition ($K_{150}$, $K_{19}$). For the NIH/3T3 cells (FIG. 12), expression levels obtained by surface associated complexes with 28, 426, and 853 biotin was significantly greater than that obtained with complexes containing 1705 biotin residues (p<0.05). No significant difference between complexes with 28 biotin groups and its bulk control (p>0.05) and 1705 biotin groups and its bulk control (p>0.05) were found. The distribution of transfected cells throughout the cell population also differed between the delivery mechanisms. For bulk delivery, transfected cells were seen throughout the cell population (not shown); however, surface-mediated delivery resulted in cells that were transfected in clusters. Additionally, the location of transfected cells on the surface was consistent with the location of surface-associated DNA seen with the fluorescently-tagged plasmid.

Figure 13:
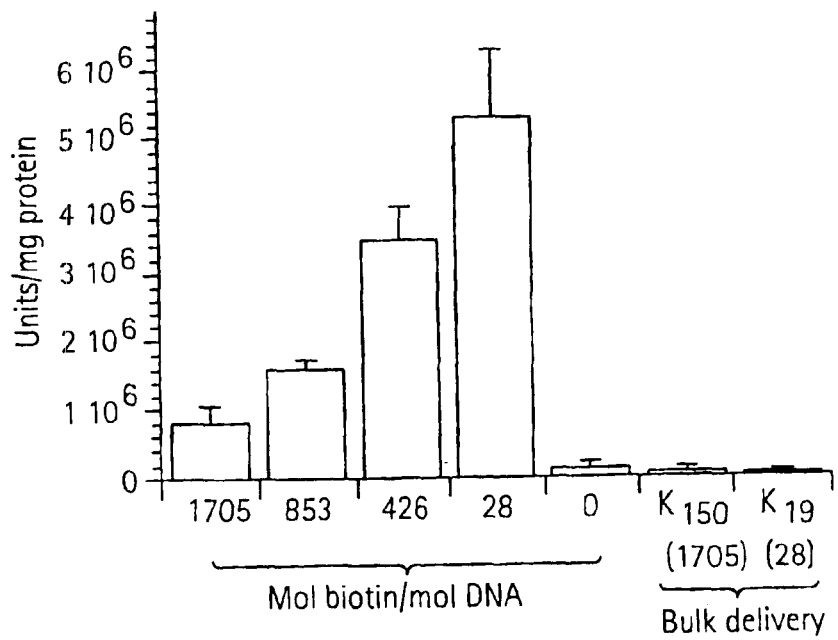
FIG. 13 shows expression levels achieved by surface mediated transfection after 96 hours of incubation for HEK293T cells.
Figure 14:
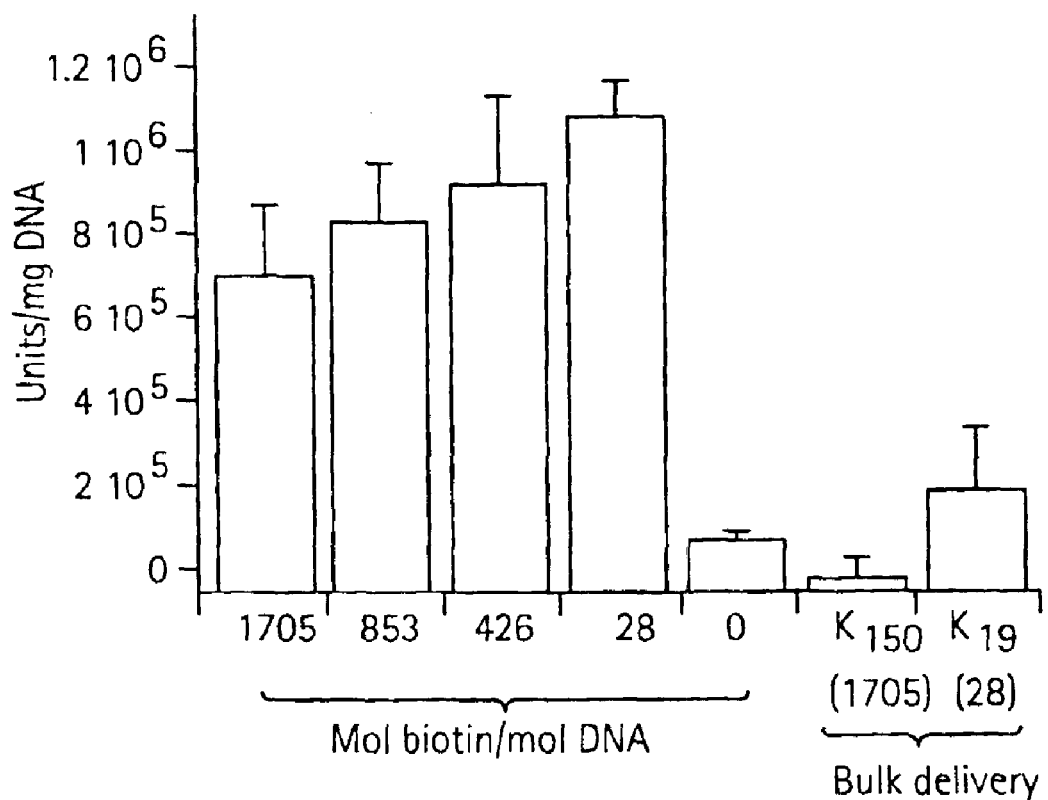
FIG. 14 shows expression levels achieved by surface mediated transfection after 96 hours of incubation for NIH/3T3.

The expression levels of protein at 96 hrs by cells cultured on DNA-modified surfaces increased relative to the that observed at 48 hours and, for all biotinylated DNA complexes, was greater than that obtained by bulk delivery. Maximal expression levels by HEK293T cells was obtained for the complexes containing 28 biotin groups and was statistically significant from all other conditions tested (p<0.05) (FIG. 13). The expression level decreased as the average number of biotin groups on the complex increased (p<0.05). The complexes formed with $K_{150}$-B (1705 biotin groups) had the lowest transfection level of the surface associated delivery; however, the expression level was significantly greater than the bulk control (p<0.01). The expression levels for the NIH/3T3 cells were less dependent on the number of biotin groups, yet the decreasing expression levels for increasing numbers of biotin groups was again observed (FIG. 14). For all conditions tested with surface associated delivery of DNA complexes tethered to the surface with biotin groups, an increased level of transfection was observed relative to the delivery of non-biotinylated DNA complexes and the bulk delivery of DNA complexes (p<0.01).

EXAMPLES

Example 1

Use of Tethered PLL/DNA Complexes

Experiment 1

Figure 3:
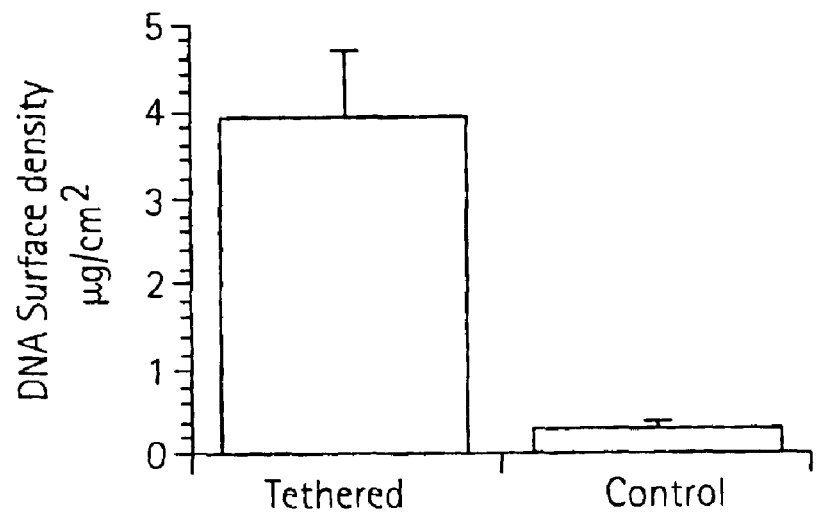
FIG. 3 shows the quantity of surface associated DNA obtained following trypsinization of the slide.

Plasmid DNA encoding either green fluorescent protein (GFP) or luciferase was complexed with modified poly-L-lysine (PLL) at a ratio of 3.1. PLL was modified by PLL reaction with the bifunctional cross-linker sulfosuccinimidyl 6-[3'-(2-pyridyldithio)-propionamido]hexanoate (Sulfo-LC-SPDP, Pierce) prior to DNA complexation at a 1:1 molar ratio. The PLL/DNA complexes were subsequently incubated with glass slides that were modified with (3-mercaptopropyl)-trimethoxysilane (MPTS, Sigma) to create pendant thiol groups. Following coupling of PLL/DNA complexes to the slide, the surfaces were extensively washed and treated with trypsin to degrade the PLL and release the DNA into solution. The surface density of DNA was determined to be $3.9\pm0.78$ $\mu g/cm^2$. Control slides incubated with PLL/DNA complexes without the sulfo-LC-SPDP tether had a surface density of $0.3\pm0.1$ $\mu g/cm^2$ (FIG. 3).

Experiment 2

Figure 4:
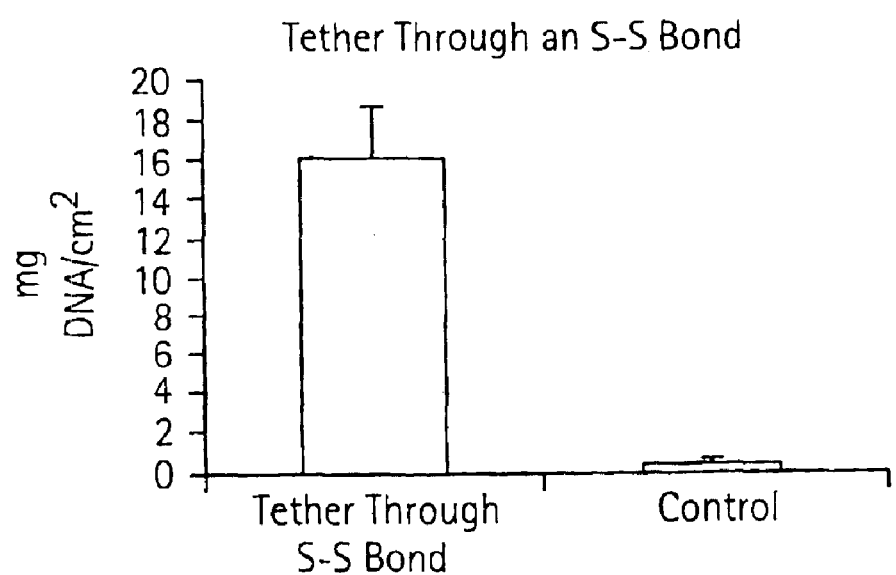
FIG. 4 shows the surface density of tethered DNA/Poly-Lysine-Cys complexes.

Glass surfaces were prepared with pendant disulfide groups by initially coupling MPTS to create pendant thiol groups. The thiol groups were then reacted with dipyridyldisulfide to form pendant disulfide groups on the surface. Plasmid DNA encoding GFP was mixed for 30 minutes with PLL at a charge ratio of 1:1 (positive to negative). The polylysine chains in the PLL/DNA complexes was covalently coupled to cysteine (which had a protected amino group) using EDC and Sulfo-NHS. The PLL/DNA complex was subsequently tethered to the glass slide through the thiol group on the attached cysteine. The glass slides were washed to remove non-specifically bound complexes. To verify attachment of the PLL/DNA complexes, the slides were then treated with trypsin to degrade the PLL and release the DNA into solution. This quantity of DNA in solution was measured using the Hoechst 33258 fluorometric dye. The amount of DNA released into solution was equal to $17.8\pm3.51$ $\mu g$, which corresponds to a surface density of $3.93\pm0.78$ (FIG. 4). The efficiency of incorporation was determined to be $13.8\pm2.7\%$. Control slides in which cysteine was not complexed to DNA released $0.63\pm0.18$ $\mu g$, which corresponds to a surface density of $0.28\pm0.08$ $\mu g/cm^2$. The amount of DNA tethered to the slides was consistent with the amounts typically used in transfections. The integrity of the released DNA was subsequently analyzed by gel electrophoresis and found to be intact.

NIH3T3 cells were plated into the well of the 96 well dish containing the tethered DNA prepared as described above. Cells were cultured at 37° C. At various times, the cells were examined using a fluorescence microscope for the expression of GFP. Transfected cells were observed within the wells of the dish.

Experiment 3

Tethered DNA complexes were attached to 96 well polystyrene microtiter plates with a streptavidin coating as follows: PLL was reacted with the bifunctional cross-linker sulfo-NHS-LC-Biotin (Pierce) prior to DNA complexing at a 1:1 or 10:1 molar ratio (Biotin:PLL), generating biotinylated PLL. To form the complexes, biotinylated PLL was mixed with DNA at a charge ratio of 3:1 and allowed to self-assemble for 30 minutes. The complexes are formed such that the biotin groups are available for specific coupling to a surface through a streptavidin-biotin interaction. These complexes were subsequently incubated (1–2 hours) in streptavidin modified 96-well plates. Following coupling of PLL/DNA complexes to the wells, the surfaces were extensively washed with TNBS buffer and treated with trypsin to degrade the PLL and release the DNA into solution. The number of biotin groups available for coupling controlled the surface density of DNA. Experiments using 200, 100, and 50 moles biotinylated PLL/moles DNA and the 1:1 molar ratio (Biotin:PLL) PLL, yielded the following surface densities: $1.16\pm0.01$ $\mu g/cm^2$, $2.54\pm0.05$ $\mu g/cm^2$, $2.17\pm0.08$ $\mu g/cm^2$ respectively. Similar experiments with the 10:1 molar ratio yielded surface densities of $2.14\pm0.16$ $\mu g/cm^2$, $0.32\pm0.05$ $\mu g/cm^2$, and $0.41\pm0.06$ $\mu g/cm^2$. Control slides incubated with PLL/DNA complexes without the sulfo-LC-Biotin tether had a surface density of $0.06\pm0.02$ $\mu g/cm^2$.

Example 2

Synthesis of Biotinylated Poly-Lysine

Plasmid DNA encoding for β-galactosidase (pNGVL1-β-gal) was purified from bacteria culture using Qiagen (Santa Clara, Calif.) reagents and stored in Tris-EDTA buffer solution (10 mM Tris, 1 mM EDTA, pH=7.4). Fluorescein tagged β-galactosidase vector (Fl-β-gal) was purchased from Gene Therapy Systems (San Diego, Calif.). Two polylysine (PLL) peptides were used for DNA complexation: Cys-Trp-Lys$_{19}$ ($K_{19}$, BioPeptide, San Diego, Calif.) and Lys$_{150}$ ($K_{150}$, average molecular weight of 20,000, Sigma, St Louis, Mo.). Avidin and biotin reagents for peptide modification and surface tethering were purchased from Pierce (Rockford, Ill.). All other reagents were obtained from Fisher Scientific (Fairlawn, N.J.) unless otherwise noted.

Peptide $K_{19}$ was modified with a biotin group through the terminal cysteine residue by reaction of the sulfhydryl group with the iodoacetyl group of the biotinylation reagent, EZ-link-PEO-Iodoacetyl-Biotin. $K_{19}$ (10 mg) was dissolved in 850 $\mu L$ of buffer (50 mM Tris, 5 mM EDTA, pH=8.3) that was previously bubbled with nitrogen gas. The EZ-link-PEO-Iodoacetyl-Biotin (3.8 mg) was also dissolved in 150 $\mu L$ of buffer (0.1 M Sodium Phosphate, 5 mM EDTA, pH=6.0). The biotin solution was added dropwise to the peptide solution, mixed gently, covered with aluminum foil and incubated for 90 minutes. The starting peptide solution and the reaction mixture were analyzed by HPLC to determine if the reaction had gone to completion. The starting peptide solution and the reaction mixture were resolved by injecting 20 $\mu g$ through a C18 RP-HPLC column eluted with water (0.1% trifluoroacetic acid (TFA)) and a acetonitrile gradient (0.1% TFA, 0 to 95% over 50 minutes at 60° C.) while detecting the absorbance at 260 nm. For purification, sephadex (G15) was equilibrated in deionized water for 30 minutes prior to packing in a glass column (2 cm diameter× 12 cm height). The reaction mixture was passed through the column using deionized water. Twenty fractions were collected and the presence of the tryptophan side chain was examined by measuring the absorbance at 260 nm (Beckman Instruments Inc., Fullerton, Calif.). The fractions with the greatest absorbance at 260 nm were lyophilized (Labconco Corp., Kansas City, Mo.) and analyzed by mass spectrometry. The purified biotinylated peptide ($K_{19}$-B) was stored as a powder at −20° C.

Peptide $K_{150}$ was biotinylated using succinimide ester (NHS)/amine chemistry. $K_{150}$ (10 mg) was dissolved in 1 mL of phosphate buffered saline (PBS, pH=7) and EZ-link-Sulfo-NHS-LC-Biotin (2.8 mg) was added directly to the solution, mixed gently and incubated for 2 hours at 4° C. The reaction mixture was purified using dialysis cassettes immersed in deionized water. The dialyzed product was further purified using a monomeric avidin column to separate the biotinylated components from non-biotinylated species. The biotinylated product was eluted with 10 ml of a 10 mM biotin solution and dialyzed to remove the unconjugated biotin. The purified biotinylated peptide ($K_{150}$-B) was then lyophilized and stored as a powder at −20° C. The degree of biotinylation of $K_{150}$-B was determined by quantifying the mole ratio of biotin to $K_{150}$ using 2[4'-hydroxyazobenzene]-benzoic acid (HABA). The absorbance at 500 nm of a HABA/avidin solution in PBS was recorded before and after the addition of the $K_{150}$-B and used to calculate the molar ratio of biotin to $K_{150}$.

Example 3

Complex Formation and Surface Tethering

The ability of the biotinylated and non-biotinylated polylysine ($K_{150}$, $K_{150}$-B, $K_{19}$, $K_{19}$-B) synthesized as described above, to condense DNA was assessed by gel electrophoresis. Biotinylated and non-biotinylated peptides were mixed and added in a stepwise manner (1 μL of 1 mg/mL) to a DNA solution (200 μL of 20 μg/mL). After each addition step, the solution was vortexed for 4 seconds, incubated for 10 min and a sample (10 μL) removed. Upon complete addition of peptide, trypsin was added to digest the polylysine. Gel electrophoresis was performed to assess the extent of complex formation for the samples and the trypsin-digested DNA solution.

DNA/PLL complexes were incubated on surfaces to specifically tether the complexes through the biotin-neutravidin binding. DNA (90 μL of 44.4 μg/mL) was complexed at a charge ratio (+/−) of 5.5:1 with the four peptides ($K_{150}$, $K_{150}$-B, $K_{19}$, or $K_{19}$-B) individually or with mixtures of biotinylated and non-biotinylated peptides. The number of tethers on each complex is varied by mixing biotinylated and non-biotinylated PLLs prior to complexation with DNA. Complexes were incubated after mixing for 30 min at room temperature and then allowed to bind to pre-washed neutravidin coated surfaces for 2 hours. The unbound complexes were then removed from the wells and washed with tris-buffered saline (TBS). The surface quantities of DNA were determined by incubating with trypsin (100 μL) at 37° C. for 2 hours to degrade the PLL and release the DNA into solution. The quantity of DNA was measured with a fluorometer (Turner Designs TD-360) using the Hoechst dye. Tethered DNA complexes were visualized by fluorescence microscopy using the Fl-β-gal vector before and after washing with TBS.

Example 4

Cell Culture and Transfection

Transfection of cells on the DNA-modified surfaces, produced as described above, was examined using a β-galactosidase plasmid and two cell lines (HEK293T and NIH/3T3). Polyethyleneimine (PEI, 22 kDa, MBI-Fermentas, Hanover, Md., 0.5 μL of 10 μM) was added to DNA-modified surfaces and incubated for 5 min. Cells were then plated and cultured on the surfaces for 48–96 hours and then lysed for assay of β-galactosidase enzyme activities (Promega, Madison, Wis.) and protein levels (BioRad, Hercules, Calif.). Alternatively, cells were stained with X-gal to determine the location of transfected cells. HEK293T and NIH/3T3 were cultured at 37° C. and 5% $CO_2$ in Dulbecco's modified eagle medium (DMEM, Life Technologies, Gaithersburg, Md.) supplemented with 10% heat inactivated FBS and 1% penicillin/streptomycin. Control experiments to characterize the effectiveness of surface-mediated delivery were performed by using bulk delivery of DNA complexed with the non-biotinylated $K_{150}$ or $K_{19}$. For bulk delivery of $K_{150}$/DNA complexes, the quantity of DNA delivered was determined based on the amount of surface associated DNA obtained when DNA was complexed only with $K_{150}$-B. For bulk delivery of $K_{19}$/DNA, the quantity of DNA delivered was determined based on the amount of surface-associated DNA obtained when DNA was complexed with a mixture of $K_{150}$-B/$K_{19}$, which had a predominance of $K_{19}$ over $K_{150}$-B. For the bulk delivery experiments, HEK293T and NIH3T3 cells were plated at one day prior to transfection and cultured in complete media.

The present invention is not to be limited in terms of the particular embodiments described in this application, which are intended as single illustrations of individual aspects of the invention. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims. The contents of each reference, patent and patent application cited in this application is hereby incorporated by reference in its entirety.

What is claimed is:

1. A controlled nucleic acid delivery system, comprising nucleic acid-polylinker complexes immobilized to a support substrate, wherein said complexes are formed prior to attachment to the solid support, and wherein the nucleic acid-polylinker complex is capable of being delivered to cells cultured on the support substrate.

2. The controlled nucleic acid delivery system of claim 1, wherein the nucleic acid-polylinker complexes are immobilized to the surface of a support substrate by a functional group attached to the polylinker.

3. The controlled nucleic acid delivery system of claim 2, wherein the complexes may be covalently or non-covalently immobilized.

4. The controlled nucleic acid delivery system of claim 3, wherein a percentage of the polylinker in the complexes is covalently attached to the support substrate and the remaining polylinker is bound to the nucleic acid but is not directly attached to the support substrate.

5. A controlled nucleic acid delivery system comprising nucleic acid-polylinker complexes, said complexes covalently or non-covalently immobilized to the surface of a support substrate by a functional group attached to the polylinker, wherein a percentage of the polylinker in the complexes is covalently attached to the support substrate and the remaining polylinker is bound to the nucleic acid but is not directly attached to the support substrate, and wherein the percentage of polylinker covalently attached to the support substrate is more than 0.2%, and wherein the nucleic acid-polylinker complex is capable of being delivered to cells cultured on the support substrate.

6. The controlled nucleic acid delivery system of claim 5, wherein the covalent bond is broken after a cell is plated on the surface of the support substrate.

7. The controlled nucleic acid delivery system of claim 3, wherein a percentage of the polylinker in the complexes is non-covalently attached to the support substrate and the remaining polylinker is bound to the nucleic acid but is not directly attached to the support substrate.

8. The controlled nucleic acid delivery system of claim 7, wherein the complexes are formed by condensation of the nucleic acid with a polylinker chemically modified by a functional group that promotes attachment to the support substrate.

9. The controlled nucleic acid delivery system of claim 7, wherein the complexes are formed by condensation of the nucleic acid with a polylinker not chemically modified by a functional group.

10. The controlled nucleic acid delivery system of claim 7, wherein the complexes are formed by condensation of the nucleic acid with a mixture of non-chemically modified polylinker and chemically modified polylinker.

11. The controlled nucleic acid delivery system of claim 1, wherein the nucleic acid is DNA, RNA, or an oligonucleotide.

12. A controlled nucleic acid delivery system comprising nucleic acid-polylinker complexes immobilized to a support substrate, wherein the nucleic acid is DNA, RNA, or an oligonucleotide, and wherein the oligonucleotide is an antisense oligonucleotide or a catalytic RNA capable of interfering with the expression of a gene, and wherein the nucleic acid-polylinker complex is capable of being delivered to cells cultured on the support substrate.

13. The controlled nucleic acid delivery system of claim 1, wherein the polylinker is a cationic polymer, cationic lipid, cationic protein, or cationic peptide.

14. The controlled nucleic acid delivery system of claim 1, wherein the support substrate of the invention is selected from the group consisting of glass, peptide polymers, collagen, peptoid polymers, polysaccharides, carbohydrates, hydrophobic polymers, polymers, tissue culture polystyrene, planar lipid layers, planar lipid bilayers, metals, derivatized plastic films, glass beads, plastic beads, alumina gels, magnetic beads, nitrocellulose, cellulose, nylon membranes, cotton, and glass wool.

15. The controlled nucleic acid delivery system of claim 1, wherein nucleic acid delivery is controlled through (i) complex density at the surface of the support substrate, (ii) complex location on the surface of the support substrate, and (iii) the number of bonds linking the polylinkers in a complex to the solid support.

16. The method of claim 15 wherein the linkages between the polylinker and the support substrate are reversible.

17. The controlled nucleic acid delivery system of claim 15, wherein complex density ranges from 0.01 to 10.0 $\mu$g DNA/cm$^2$.

18. The controlled nucleic acid delivery system of claim 15, wherein the polylinker is noncovalently bonded to the support substrate.

19. The controlled nucleic acid delivery system of claim 1, wherein delivery of the nucleic acid-polylinker complex is through cell internalization of the released complex.

20. A method of making the controlled nucleic acid delivery system of claim 1, comprising:
(a) contacting a nucleic acid with polylinkers; wherein the nucleic acid complexes with the polylinkers to form a condensed nucleic acid; and
(b) immobilizing the polylinker present in the complex to a support substrate,
wherein delivery of the nucleic acid to a cell is controlled by (i) density and location of the complex on the surface of the support substrate, and (ii) the number of bonds linking the polylinkers in a complex to the solid support, wherein a desired release rate is achieved.

21. The method of claim 20, wherein the attachment of the polylinker to the support substrate is reversible.

22. A method of making a controlled nucleic acid delivery system, comprising nucleic acid-polylinker complexes immobilized to a support substrate, wherein the nucleic acid-polylinker complex is capable of being delivered to cells cultured on the support substrate, said method comprising:
a) contacting a nucleic acid with polylinkers; wherein the nucleic acid complexes with the polylinkers to form a condensed nucleic acid; and
b) immobilizing the polylinker present in the complex to a support substrate,
wherein delivery of the nucleic acid to a cell is controlled by (i) density and location of the complex on the surface of the support substrate, and (ii) the number of bonds linking the polylinkers in a complex to the solid support, wherein a desired release rate is achieved; and
wherein the polylinkers are modified with a first functional group prior to step (a) and wherein the support substrate is modified with a second functional group capable of interacting with the first functional group.

23. The method of claim 20, wherein the nucleic acid is contacted with a mixture of modified and unmodified polylinkers.

24. A method of making a controlled nucleic acid delivery system, comprising nucleic acid-polylinker complexes immobilized to a support substrate, wherein the nucleic acid-polylinker complex is capable of being delivered to cells cultured on the support substrate, said method comprising:
a) contacting a nucleic acid with polylinkers; wherein the nucleic acid complexes with the polylinkers to form a condensed nucleic acid; and
b) immobilizing the polylinker present in the complex to a support substrate,
wherein delivery of the nucleic acid to a cell is controlled by (i) density and location of the complex on the surface of the support substrate, and (ii) the number of bonds linking the polylinkers in a complex to the solid support, wherein a desired release rate is achieved; and
wherein the polylinkers are modified with a first functional group prior to step (a) and wherein the support substrate is modified with a second functional group capable of interacting with the first functional group, and wherein the polylinker is poly-L-lysine (PLL), the first functional group is biotin, and the second functional group is avidin or an avidin derivative.

25. A method of spatially controlling the delivery of a nucleic acid to a cell comprising:
(a) modifying a polylinker with a first functional group;
(b) contacting a nucleic acid with modified polylinker; wherein the nucleic acid complexes with the polylinker to form a condensed nucleic acid; and
(c) immobilizing the nucleic acid-polylinker complex to a surface of a support substrate, wherein the surface of the support substrate is modified with a second functional group capable of interacting with the first functional group, and wherein complexes formed with modified polylinker are specifically bound to the support surface, and wherein the specific binding of the complexes to the surface of the support substrate is located at specific regions of the substrate in a defined pattern.

26. The method of claim 25, wherein the nucleic acid is contacted with modified and unmodified polylinker in step (a) and wherein the unmodified polylinker is ionically bound to the nucleic acid but is not bound to the support surface in step (c).

27. The method of claim 26, wherein the substrate is a microtiter plate comprising multiple wells.

28. A method of temporally controlling the delivery of a nucleic acid to a cell population comprising:
(a) modifying a polylinker with a first functional group;
(b) contacting a nucleic acid with modified polylinker; wherein the nucleic acid complexes with the polylinker to form a condensed nucleic acid; and
(c) immobilizing the nucleic acid-polylinker complex to a surface of a support substrate, wherein the surface of the support substrate is modified with a second functional group capable of interacting with the first functional group, and wherein complexes formed with modified polylinker are specifically bound to the support surface, and wherein the specifically bound complexes are released at desired times and internalized by a cell adhering to the surface of the support substrate.

29. A method of temporally and spatially controlling the delivery of a nucleic acid to a cell population comprising:

(a) modifying a polylinker with a first functional group;

(b) contacting a nucleic acid with modified polylinker; wherein the nucleic acid complexes with the polylinker to form a condensed nucleic acid; and (c) immobilizing the nucleic acid-polylinker complex to a surface of a support substrate, wherein the surface of the support substrate is modified with a second functional group capable of interacting with the first functional group, and wherein complexes formed with modified polylinker are specifically bound to the support surface and located at specific regions of the substrate in a defined pattern, and wherein the specifically bound complexes are released at desired times and internalized by a cell adhering to the surface of the support substrate.

* * * * *